United States Patent
Poulsen

(10) Patent No.: US 8,097,584 B2
(45) Date of Patent: Jan. 17, 2012

(54) STABILIZED FORMULATIONS OF INSULIN THAT COMPRISE ETHYLENEDIAMINE

(75) Inventor: Christian Poulsen, Copenhagen K (DK)

(73) Assignee: Novo Nordisk A/S, Bagsvaerd (DK)

( * ) Notice: Subject to any disclaimer, the term of this patent is extended or adjusted under 35 U.S.C. 154(b) by 176 days.

(21) Appl. No.: 11/914,567

(22) PCT Filed: May 22, 2006

(86) PCT No.: PCT/EP2006/062491
§ 371 (c)(1),
(2), (4) Date: Jun. 6, 2008

(87) PCT Pub. No.: WO2006/125763
PCT Pub. Date: Nov. 30, 2006

(65) Prior Publication Data
US 2008/0267907 A1    Oct. 30, 2008

Related U.S. Application Data

(60) Provisional application No. 60/685,827, filed on May 31, 2005.

(30) Foreign Application Priority Data

May 25, 2005   (EP) .................................... 05104480

(51) Int. Cl.
*A61K 38/28* (2006.01)
*C07C 211/00* (2006.01)
(52) U.S. Cl. ..................... 514/3; 514/4; 585/4; 530/303
(58) Field of Classification Search .................. None
See application file for complete search history.

(56) References Cited

U.S. PATENT DOCUMENTS

| | | | |
|---|---|---|---|
| 4,605,513 A | 8/1986 | DiMarchi | |
| 4,839,341 A | 6/1989 | Massey et al. | |
| 4,892,817 A | 1/1990 | Pawlak | |
| 5,446,024 A | 8/1995 | Builder et al. | |
| 5,750,497 A | 5/1998 | Havelund et al. | |
| 5,783,556 A * | 7/1998 | Clark et al. ........................ | 514/4 |
| 5,898,067 A | 4/1999 | Balschmidt et al. | |
| 6,005,081 A | 12/1999 | Burton et al. | |
| 6,034,054 A | 3/2000 | DeFelippis et al. | |
| 6,211,144 B1 | 4/2001 | Havelune | |
| 7,384,914 B2 * | 6/2008 | Goldberg et al. ................. | 514/3 |
| 2001/0031726 A1 | 10/2001 | Van Antwerp et al. | |
| 2003/0125234 A1 | 7/2003 | Middaugh | |
| 2006/0183683 A1 | 8/2006 | Hansen et al. | |

FOREIGN PATENT DOCUMENTS

| | | |
|---|---|---|
| WO | WO 01/37856 | 5/2001 |
| WO | WO 2002/098445 | 12/2002 |
| WO | WO 2004/007520 | 1/2004 |
| WO | WO 2004/060310 | 7/2004 |
| WO | WO 2004/112828 | 12/2004 |

OTHER PUBLICATIONS

Poulsen et al., Pharmaceutical Reseasrch, Nov. 2008, 25:11:2534-44.*

Wang, Wei, Protein aggregation and its inhibition in biopharmaceutics, International Journal of Pharmaceutics, vol. 289, pp. 1-30 (2005).

Brange, J. et al., Chemical Stability of Insulin 2. Formation of Higher Molecular Weight Transformation Products During Storage of Pharmaceutical Preparations,, Pharmaceutical Research, vol. 9 (6), pp. 727-734 (1992).

Office Action in U.S. Appl. No. 11/914,564, mailed from the USPTO on Oct. 29, 2009.

Non-Final Office Action mailed from the USPTO on Jul. 9, 2010 in U.S. Appl. No. 11/914,564, (filed Nov. 16, 2007 by Poulsen).

* cited by examiner

*Primary Examiner* — Lorraine Spector
(74) *Attorney, Agent, or Firm* — Michael J. Brignati

(57) ABSTRACT

The present invention relates to a pharmaceutical formulation comprising insulin, an insulin analogue or an insulin derivate and ethylenediamine or salts thereof and an antimicrobial preservative agent.

10 Claims, 3 Drawing Sheets

STABILIZED FORMULATIONS OF INSULIN THAT COMPRISE ETHYLENEDIAMINE

CROSS-REFERENCE TO RELATED APPLICATIONS

This application is a 35 U.S.C. §371 national stage application of International Patent Application PCT/EP2006/062491 (published as WO 2006/125763), filed May 22, 2006, which claimed priority of European Patent Application 05104480.8, filed May 25, 2005; this application further claims priority under 35 U.S.C. §119 of U.S. Provisional Application 60/685,827, filed May 31, 2005.

FIELD OF THE INVENTION

The present invention relates to a pharmaceutical formulation with improved chemical stability and a method for improving the chemical stability of a polypeptide in a purification process or in a pharmaceutical formulation.

BACKGROUND OF THE INVENTION

Polypeptide instability during storage or production of pharmaceutical formulations as well as during purification processes is a well-known problem. Chemical instability in form of formation of soluble aggregates of the polypeptide (covalent dimers and polymers), deamidation, oxidation and isomerisation etc. are well known problems difficult to avoid due to the relatively labile nature of most polypeptides. Chemical instability of polypeptides in pharmaceutical formulations therefore causes significant problems for production and storage of polypeptide pharmaceuticals and methods for reduction or elimination of this problem are of considerable interest to the pharmaceutical industry. Formation of such chemical degradation products is often accelerated with increasing temperature; hence restrictions regarding exposure to elevated temperatures (i.e. above for instance 8° C.) during distribution, storage and use are often necessary to ensure sufficient quality of the pharmaceutical polypeptide. As a consequence, the patient must often store the protein/peptide pharmaceutical in the fridge to depress the inevitable accelerated chemical degradation at room temperature.

Among the various chemical degradation pathways of pharmaceutical polypeptides, special attention is often paid to aggregation due to the reduced biological potency and potential antigenic properties associated with such aggregated forms. Some aggregates involve formation of new covalent bond(s) for instance through disulfide-bond formation between free Cysteine residues, transamidation, dityrosine formation or formaldehyde-mediated crosslinking (see also Wang, W. Int. J. Pharm. 289:1-30, 2005). Transamidation concerns reaction between free amino groups (eg. N-terminals) from one polypeptide with amide groups (Asparagine or Glutamine residues) of another polypeptide. Formation of transamidation dimers and polymers in insulin formulation have been reported by Brange and co-workers (Brange, J. Pharm Res 9:727-734, 1992).

In pharmaceutical formulations of insulin, reduction of the formation of covalent dimers and polymers are of particular interest due to their markedly reduced biological potency compared to the native insulin molecule and to their potential antigenic properties. Consequently, insulin formulations stabilized against chemical degradation, in particular formation of covalent dimers and polymers, are highly desirable.

The addition of buffers to polypeptide-containing pharmaceutical solutions is essential in order to stabilize pH of the purification or pharmaceutical solution within a desired pH range. Conventionally, phosphate buffers have been used as the preferred buffering agent for pharmaceutical formulations containing polypeptides.

US20030125234 discloses alteration of protein physical stability (formation of insoluble aggregates or fibrils) by multiple charged compounds. Ethylenediamine and insulin are presented, however, no significant positive effect on physical stability of insulin is observed in the presence of ethylenediamine. Chemical stability (e.g. formation of soluble aggregates, e.g. covalent dimer and polymer), which is the topic of the present invention, is not evaluated.

SUMMARY OF THE INVENTION

It has been found that pharmaceutical polypeptide formulations having increased chemical stability can be obtained by adding ethylenediamine or salts thereof as a buffer to said formulation.

Thus in one aspect the present invention is related to a pharmaceutical formulation comprising a polypeptide and ethylenediamine or salts thereof and an antimicrobial preservative agent.

In another aspect the invention is related to a method for improving the stability of a polypeptide in a purification process. The method will comprise addition of an adequate amount of ethylenediamine or a salt thereof as a buffer to the solution containing the polypeptide to be purified.

BRIEF DESCRIPTION OF THE DRAWINGS

In FIG. 5 acyl1 means the acylated insulin B29-N$^\epsilon$-(N-litocholyl-γ-glytamyl)-des(B30)-human insulin, acyl2 means the acylated insulin Lys$^{B29}$(N$^\epsilon$-hexadecandioyl-γ-Glu)-des (B30) human insulin) and acyl3 means the acylated insulin B29-N$^\epsilon$-tetradecanoyl-des(B30)-human insulin.

DESCRIPTION OF THE INVENTION

Figure 1:
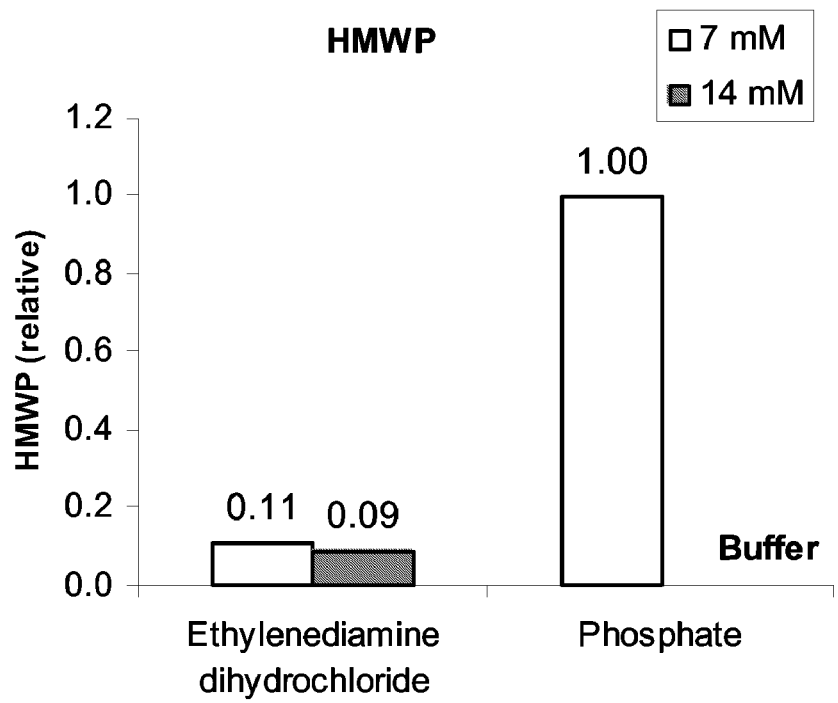
FIG. 1 shows the results from the gel permeation chromatography HPLC (GPC-HPLC) analyses of the chemical stability of a polypeptide (insulin aspart) in compositions containing ethylenediamine dihydrochloride or phosphate as buffer, measured as relative content of high molecular weight protein (% HMWP) after 3 months storage at 37° C.

The invention is related to stabilization of pharmaceutical peptide formulations and solutions comprising a peptide. The term "stabilized solution" refers to a polypeptide solution with increased chemical stability. Pharmaceutical formulations and solutions of polypeptides from various processing steps (e.g. a purification step) are examples of such solutions.

The term "chemical stability" of the protein solution as used herein refers to chemical covalent changes in the polypeptide structure leading to formation of chemical degradation products with potentially less biological potency and/or potentially increased immunogenic properties compared to the native protein structure. Various chemical degradation products can be formed depending on the type and nature of the native polypeptide and the environment to which the polypeptide is exposed. Chemical degradation can most probably not be completely avoided and increasing amounts of chemical degradation products are often seen during storage and use of the polypeptide solution as well-known by the person skilled in the art. Most polypeptides are prone to deamidation, a process in which the side chain amide group in glutaminyl or asparaginyl residues is hydrolyzed to form a free carboxylate. Other degradations pathways involve formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Transamidation concerns reaction between free amino groups (eg. N-terminals) from one polypeptide with amide groups (eg. Asparagine or Glutamine residues) of another polypeptide. Formation of transamidation dimers and polymers in insulin formulation have been reported by Brange and co-workers (Brange, J. Pharm Res 9:727-734, 1992). Oxidation (of for instance methionine residues) can be mentioned as another variant of chemical degradation. The chemical stability of the polypeptide solution can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or "hydrophobicity" using various chromatography techniques (e.g. SEC-HPLC and/or RP-HPLC).

Hence, as outlined above, a "stabilized polypeptide solution" refers to a solution with increased chemical stability. Further, as outlined above, a "stabilized formulation" refers to a formulation with increased chemical stability. In general, a formulation must be stable during use and storage (in compliance with recommended use and storage conditions) until the expiration date is reached.

The stabilization is achieved by addition of ethylenediamine to pharmaceutical formulation or solution comprising the polypeptide in question. The optimal concentration of ethylenediamine to obtain an adequate chemical stabilization of a certain polypeptide depends on various parameters such as polypeptide concentration and structure (eg. number of Asn and Gln residues per polypeptide). Hence, the molar ratio between ethylenediamine and polypeptide cannot be chosen arbitrarily to obtain an adequate chemical stabilization. In general, the molar ratio between ethylenediamine and polypeptide (ethylenediamine:polypeptide) should be at least 1:10, preferably at least 1:5, more preferably at least 2:1, more preferably at least 4:1. Obviously, the optimal ratio depends on the specific polypeptide and may vary compared to the above-mentioned ratios.

Thus the concentration of the ethylenediamine may vary within a relatively large range depending on the polypeptide in question and the other constituents in the pharmaceutical formulation. The concentration of the ethylenediamine will typically be in the range from 0.01-100 mM.

In another embodiment the concentration of ethylenediamine is between 1 and 50 mM or between 3 and 25 mM.

In a further embodiment the concentration of ethylenediamine is between 3 and 20 mM, between 4 and 20 mM, between 5 and 20 mM, between 5 and 18 mM, between 5 and 17 mM, between 5 and 16 mM.

The pH of the pharmaceutical formulation may be in the range from about 2 to about 10 but will typically be in the range from about 4 to about 8.5.

In a further embodiment the pH will be from 4.5-6.5, from 5.5.-6.5, from 6.5-9, from 6.5-8.5 or from 7-8.

One object of the present invention is to provide a pharmaceutical polypeptide formulation comprising ethylenediamine or salts thereof as a buffer compound wherein the polypeptide compound is present in a concentration from 0.01 mg/ml to 100 mg/ml.

The pharmaceutical formulation may be an aqueous formulation or a freeze-dried formulation, whereto the health care provider or the patient adds solvents and/or diluents prior to use, or it may be a dried formulation (e.g. freeze-dried or spray-dried) ready for use without any prior dissolution.

In one embodiment of the invention the pharmaceutical formulation is an aqueous formulation, i.e. a formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

A non limiting example of a pharmaceutical formulation according to the invention is an aqueous formulation wherein the concentration of the ethylenediamine is in the range from 0.01-100 mM, particularly the concentration of ethylenediamine is at most 50 mM, such as 1-50 mM, more particularly 3-25 mM and even more particularly 5-16 mM.

In one embodiment the pharmaceutical formulation may, in addition to ethylenediamine or salts thereof, further comprise one or more conventional buffers or buffer systems. Such a conventional buffer may be selected from the group consisting of sodium acetate, sodium carbonate, citric acid, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinic acid, maleic acid, fumaric acid, tartaric acid, aspartic acid and/or mixtures and/or salt thereof. The conventional buffer or buffer system will typically comprise a phosphate buffer.

In one embodiment the pharmaceutical formulation may, in addition to ethylenediamine or salts thereof, further comprise one or more buffers or buffer systems selected from the group consisting of diethylmalonic acid, trimellitic acid, shikimic acid, glycinamid hydrochloride, 2-amino-2-methyl-1,3-propanediol (AMPD) and tetraethylammonium chloride (T.E.A. chloride) or salts thereof.

In one embodiment the total concentration of buffers may be in the range from 0.01-100 mM, particularly the total concentration of the buffer is at most 50 mM, such as 1-50 mM. The optimal buffer concentration may vary slightly depending on the specific combination of buffers, e.g. as a result of different buffer capacities among the different buffers.

The pharmaceutical compositions according to the invention will further comprise one or more antimicrobial preservatives. Suitable pharmaceutically acceptable preservatives may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, thimerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof.

In one embodiment of the invention the preservative is selected from the group consisting of phenol, o-cresol, m-cresol and p-cresol and mixtures thereof, in particular phenol and m-cresol.

In a further embodiment of the invention the preservative is present in a concentration from 0.1 mg/ml to 20 mg/ml, from 0.1 mg/ml to 5 mg/ml, from 5 mg/ml to 10 mg/ml or from 10 mg/ml to 20 mg/ml. Each one of these specific preservatives constitutes an alternative embodiment of the invention.

The pharmaceutical formulation may further comprise components selected from the group consisting of stabilizer(s), amino acid base(s), antimicrobial preservative(s), chelating agent(s), surfactant(s) and tonicity agent(s).

The use of a stabilizer in pharmaceutical compositions is well-known to the skilled person. For convenience reference is made to Remington: *The Science and Practice of Pharmacy*, 19$^{th}$ edition, 1995. In one embodiment the compositions of the invention are stabilized liquid pharmaceutical compositions whose therapeutically active components include a polypeptide that possibly exhibits formation of degradation products during storage in liquid pharmaceutical formulations. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53).

Formation of degradation products of a polypeptide during storage of a liquid pharmaceutical composition can adversely affect biological activity of that polypeptide, resulting in loss of therapeutic efficacy of the pharmaceutical composition.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment, the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention, methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises an isotonic agent. Isotonic agents may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propylene glycol), 1,3-propanediol, 1,3-butanediol) polyethylene glycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. Chelating agents may be selected from salts of ethylenediamine tetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience, reference is made to Remington: *The Science and Practice of Pharmacy*, 19$^{th}$ edition, 1995.

In a further embodiment of the invention the formulation further comprises a surfactant. Surfactants may be selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, N$^\alpha$-acylated derivatives of lysine, arginine or histidine, or side-chain acylated derivatives of lysine or arginine, N$^\alpha$-acylated derivatives of dipeptides comprising any combination of lysine, arginine or histidine and a neutral or acidic amino acid, N$^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propane-sulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

In a further embodiment of the invention the formulation further comprises protease inhibitors such as EDTA (ethylenediamine tetraacetic acid) and benzamidine hydrochloride, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Chemical degradation of protein/peptide pharmaceuticals, especially at elevated temperatures, is a well known phenomenon leading to formation of various degradation products including soluble aggregates (eg. covalent dimers and polymers). This may reduce the biological potency of the pharmaceutical polypeptide and degradation products may potentially acquire unwanted antigenic properties.

In one embodiment of the invention the pharmaceutical formulation comprise a polypeptide selected from the group consisting of insulin, human growth hormone, glucagon, GLP-1, exendin-4, FVII, FXIII, a mixture of FVII and FXIII, IL-20, IL-21, IL-28a, IL-29, IL-31 and/or analogues and/or derivates thereof.

Other polypeptides may be selected among the group consisting of ACTH, corticotropin-releasing factor, angiotensin, calcitonin, IGF-1, IGF-2, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opioids and analogues thereof, superoxide dismutase, interferon, asparaginase, arginase, arginine deaminase, adenosine deaminase and ribonuclease.

With insulin as an example, formation of such soluble aggregates is highly unwanted due to their markedly reduced biological potency and their potential antigenic properties. The present invention shows that adding ethylenediamine (e.g. in form of the dihydrochloride salt) to an insulin formulation reduces the formation of covalent dimers and polymers significantly. The demonstrated reduction in formation of covalent dimers and polymers implies the potential of formulating protein/peptide pharmaceuticals with a much higher chemical stability at/above room temperature compared to the presently known formulations. It has been shown that the presence of ethylenediamine in concentrations above 0.1 mM increases the chemical stability of insulin formulations when compared to formulations comprising 7 mM phosphate buffer.

Accordingly, in a particular embodiment of the invention the stabilized polypeptide is insulin or an analogue or derivative thereof.

Insulin is a polypeptide consisting of two amino acid chains: An A chain and a B chain connected to one another by means of two disulfide bridges. Insulin can be divided into naturally occurring insulin, insulin analogues and insulin derivates but the definitions are not mutually exclusive and various molecules can meet more than one of the definitions.

Naturally occurring insulin refers to mammalian insulin—i.e. insulin molecules obtained from or identical to the insulin molecules from mammalian sources (eg. human, bovine or porcine). The A chain of naturally occurring insulin consists of 21 amino acids and the B chain of naturally occurring insulin consists of 30 amino acids. Naturally occurring insulin can be produced by extraction from pancreatic glands or by recombinant DNA techniques in various host cells.

In one embodiment the pharmaceutical formulation according to the invention is a formulation wherein the polypeptide is an insulin derivate or an insulin analogue.

Insulin analogues are analogues of naturally occurring insulin, namely human insulin or animal insulin, which differ by substitution of at least one naturally occurring amino acid residue with other amino acid residues and/or addition/deletion of at least one amino acid residue from the corresponding, otherwise identical, naturally occurring insulin. The added amino acid residues can also be those which do not occur naturally. Examples of insulin analogues are analogues of human insulin where the amino acid residue at position B28 is Asp, Lys, Leu, Val, or Ala and position B29 is Lys or Pro; or B3 is Lys and B29 is Glu; or A21 is Gly and Arg has been added to B31 and B32; or where the amino acid residues in B28-B30 have been deleted; or where the amino acid residue at B27 has been deleted; or where the amino acid residue at B30 has been deleted.

Insulin derivates are derivates of naturally occurring insulin or insulin analogues in which at least one organic molecule is bound to one or more of the amino acid residues. Examples of insulin derivates are derivates of naturally occurring insulin or insulin analogues where the organic molecule bound to the amino acid residues is a lipophilic molecule. Examples of insulin derivates where the organic molecule bound to the amino acid residues is a lipophilic molecule are B29-$N^\epsilon$-tetradecanoyl-des(B30)-human insulin, B29-$N^\epsilon$-tetradecanoyl-human insulin, B29-$N^\epsilon$-hexadecanoyl human insulin, B28-$N^\epsilon$-tetradecanoyl-Lys$^{B28}$Pro$^{B29}$ human insulin, B28-$N^\epsilon$-hexadecanoyl-Lys$^{B28}$Pro$^{B29}$ human insulin, B30-$N^\epsilon$-tetradecanoyl-Thr$^{B29}$Lys$^{B30}$ human insulin, B30-$N^\epsilon$-hexadecanoyl-Thr$^{B29}$Lys$^{B30}$-human insulin, B29-$N^\epsilon$-(N-hexadecanoyl-γ-glutamyl)-des(B30)-human insulin, B29-$N^\epsilon$-(N-litocholyl-γ-glytamyl)-des(B30)-human insulin, B29-$N^\epsilon$-(ω-carboxyheptadecanoyl)-des(B30)-human insulin, $N^\epsilon$B29-tetradecanoyl des(B30) human insulin, $N^\epsilon$B28-tetradecanoyl Lys$^{B28}$Pro$^{B29}$ human insulin, $N^\epsilon$B29-tetradecanoyl Asp$^{B28}$ human insulin and Lys$^{B29}$ ($N^\epsilon$-hexadecandioyl-γ-Glu)-des(B30) human insulin.

In another embodiment the pharmaceutical formulation according to the invention is a formulation wherein the polypeptide is an Asp$^{B28}$ analogue of human insulin.

In another embodiment the pharmaceutical formulation according to the invention is a formulation wherein the polypeptide is B29-$N^\epsilon$-tetradecanoyl-des(B30)-human insulin.

In another embodiment the pharmaceutical formulation according to the invention is a formulation wherein the polypeptide is B29-$N^\epsilon$-(N-litocholyl-γ-glytamyl)-des(B30)-human insulin.

In another embodiment the pharmaceutical formulation according to the invention is a formulation wherein the polypeptide is Lys$^{B29}$($N^\epsilon$-hexadecandioyl-γ-Glu)-des(B30) human insulin.

In another aspect the invention is related to a method for improving the stability of a polypeptide during processing such as a purification process. The method will comprise addition of an adequate amount of ethylenediamine or a salt thereof to the solution containing the polypeptide to be purified.

The ethylenediamine will typically be added in the last 2 or 3 purification steps (the polishing steps). The purification steps may be ion exchange chromatography, HPLC chromatography, ultrafiltration or diafiltration or other buffer exchange processes.

EXAMPLES

Example 1

Aqueous solutions containing insulin aspart (Asp$^{B28}$ human insulin) were prepared by mixing sub-solutions, containing the individual components (including the buffer component), followed by pH-adjustment by addition of diluted hydrochloric acid or sodium hydroxide to give compositions as displayed in Table 1.

TABLE 1

Example of Composition

| Component | Concentration | Main Function |
|---|---|---|
| Asp$^{B28}$ human insulin (nmol/mL) | 600 | Active Ingredient |
| Zinc (μg/mL) | 19.6 | Stabilizer |
| Phenol (mg/mL) | 1.50 | Preservative Agent |
| m-Cresol (mg/mL) | 1.72 | Preservative Agent |
| Glycerol (mg/mL) | 16 | Tonicity Agent |
| Sodium chloride (mg/mL) | 0.58 | Tonicity/Stabilizing Agent |
| Buffer (mM) | Varies | Buffer Agent |
| pH | 7.4 | — |

Compositions comprising the buffer component covered by the present invention were prepared according to the above-mentioned and a reference composition containing 7 mM sodium phosphate as buffer component was prepared in parallel.

Example 2

Samples of each composition were placed at elevated temperature (37° C. for up to three months) to accelerate the formation of chemical degradation products. The amount of the different chemical degradation products was assessed by gel permeation chromatography HPLC (GPC-HPLC) and reverse phase HPLC (RP-HPLC).

GPC-HPLC

HPLC column: Insulin HMWP (7.8×300 mm). Eluent: L-arginine 0.07% w/w, acetic acid (glacial) 15% w/w, acetonitrile 15% w/w and 70% w/w water. Isocratic elution with a flow rate of 0.7 mL/min. UV-detection at 276 nm.

RP-HPLC

HPLC column: LiChrosorb RP C18 (5 μm, 250×4 mm ID), Column temperature: 35° C. Eluent A: acetonitrile 7.7% w/w, sodium sulphate 2.8% w/w, phosphoric acid 0.50% w/w and water 89% w/w. Eluent B: acetonitrile 43% w/w and water 57% w/w. 0-35 min.: Isocratic with A/B=57/43, 35-40 min.: Linear change to A/B=20/80, 40-45 min.: Isocratic with A/B=20/80, 45-46 min.: Linear change to A/B=57/43. Flow rate 1 mL/min. UV-detection at 214 nm.

Example 3

Figure 2:
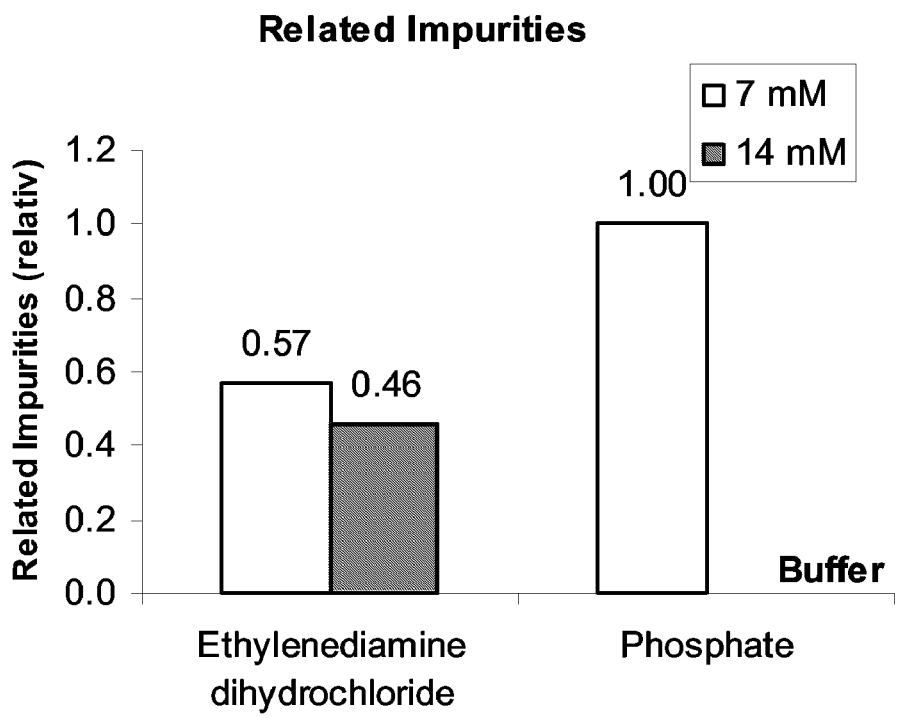
FIG. 2 shows the results from the reverse phase HPLC (RP-HPLC) analyses of the chemical stability of a polypeptide (insulin aspart) in compositions containing ethylenediamine dihydrochloride or phosphate as buffer, measured as relative content of Related Impurities after 3 months storage at 37° C.

Compositions comprising 7 or 14 mM ethylenediamine or 7 mM phosphate as buffer components were prepared following example 1 and the chemical stability of the three compositions was examined according to example 2. The results (% High Molecular Weight Proteins) from the GPC-HPLC analyses are presented in FIG. 1 and the results (% Related Impurities) from the RP-HPLC analyses are presented in FIG. 2. As can be seen the chemical stability of the polypeptide in a 7 mM ethylenediamine solution, in terms of reducing high molecular weight protein formation, is improved at least five-fold compared to 7 mM phosphate buffer.

Example 4

Figure 3:
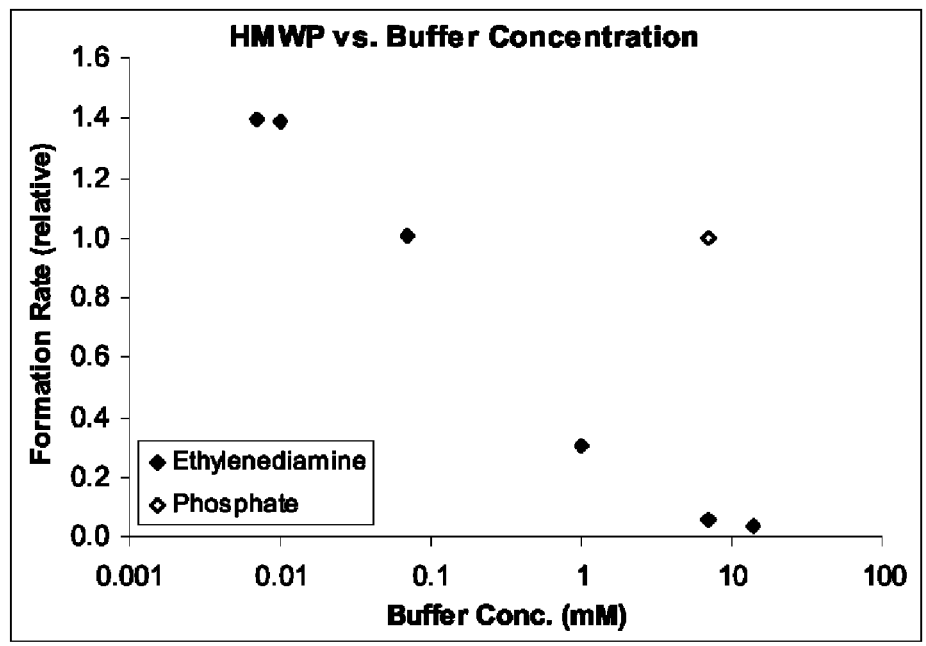
FIG. 3 shows the results from the gel permeation chromatography HPLC (GPC-HPLC) analyses of the chemical stability of a polypeptide (insulin aspart) in compositions containing 0.007 mM to 14 mM ethylenediamine dihydrochloride or 7 mM phosphate as buffer, measured as relative formation rate of high molecular weight protein (% HMWP) at 37° C.
Figure 4:
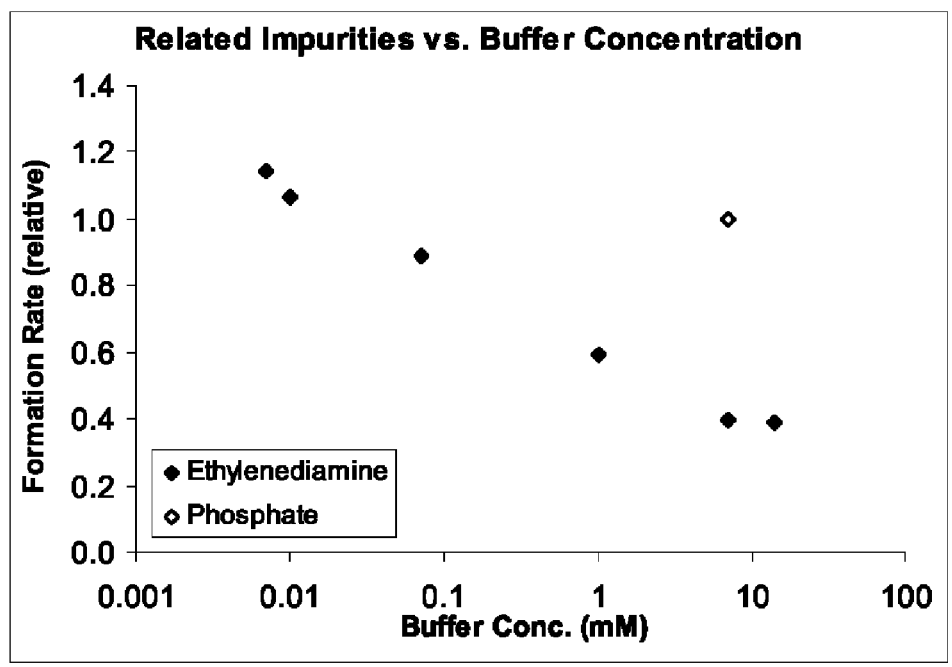
FIG. 4 shows the results from the reverse phase HPLC (RP-HPLC) analyses of the chemical stability of a polypeptide (insulin aspart) in compositions containing 0.007 mM to 14 mM ethylenediamine dihydrochloride or 7 mM phosphate as buffer, measured as relative formation rate of Related Impurities at 37° C.

Compositions comprising 0.007 mM to 14 mM ethylenediamine or 7 mM phosphate as buffer components were prepared following example 1. Each composition was placed at 37° C. and samples for chemical stability testing were pulled after 0, 6 and 12 weeks according to example 2. The results from GPC and RP-HPLC analyses in terms of formation rates of HMWP and Related Impurities, are presented in FIG. 3 and FIG. 4, respectively. As can be seen the chemical stability of the polypeptide is increased with increasing ethylenediamine concentration and superior chemical stability compared to the conventional 7 mM phosphate was observed at/above 0.1 mM ethylenediamine.

Example 5

Aqueous solutions containing human insulin or acylated insulin derivatives (acyl1, acyl2 and acyl3) were prepared by mixing sub-solutions, containing the individual components (including the buffer component), followed by pH-adjustment by addition of diluted hydrochloric acid or sodium hydroxide. Human insulin was formulated containing 6.7 mM buffer (phosphate or ethylenediamine) whereas the acylated insulin derivatives (acyl1, acyl2 and acyl3) were formulated containing 5 mM buffer (phosphate or ethylenediamine). The concentration of the other formulation components was similar to what is shown in table 1.

Example 6

Samples of each composition from example 5 were placed at elevated temperature (37° C. for up to approximately eight weeks) to accelerate the formation of chemical degradation products. The amount of the different chemical degradation products was assessed by gel permeation chromatography HPLC (GPC-HPLC).

GPC-HPLC

HPLC column: Insulin HMWP (7.8×300 mm). Eluent: L-arginine 0.06% w/w, acetic acid (glacial) 15% w/w, acetonitrile 25% w/w and 60% w/w water. Isocratic elution with a flow rate of 0.5 mL/min. UV-detection at 276 nm.

Example 7

Figure 5:
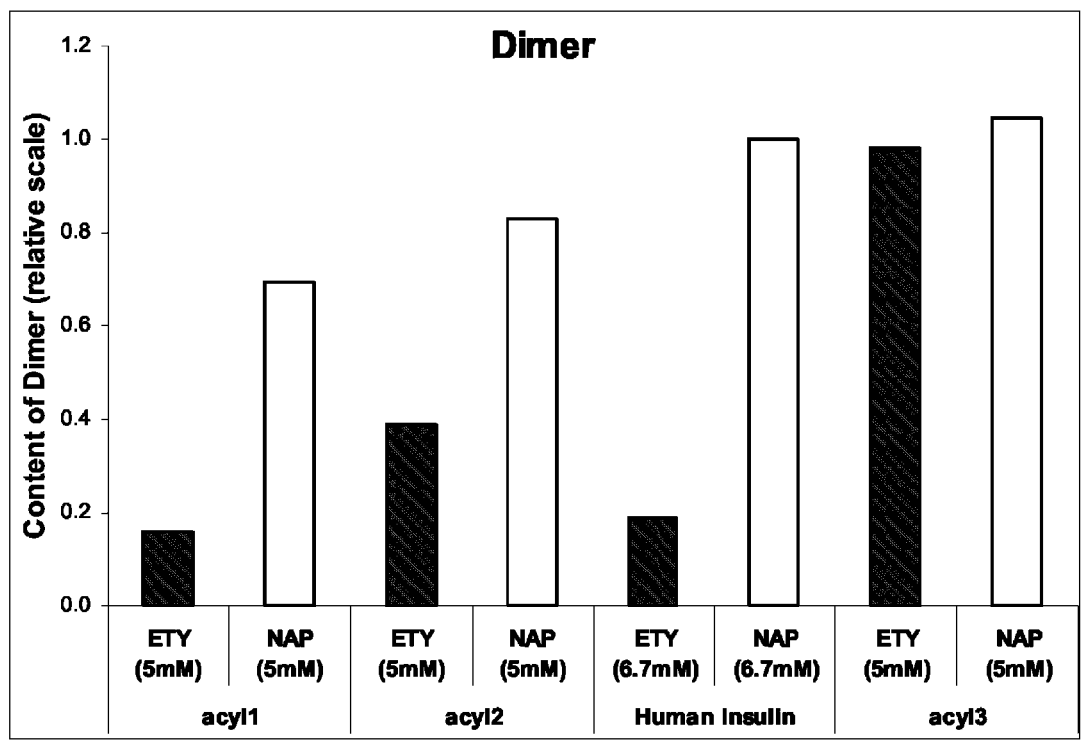
FIG. 5 shows the results from the gel permeation chromatography HPLC (GPC-HPLC) analyses of the chemical stability of polypeptides (human insulin and acylated insulin derivates) in compositions containing ethylenediamine dihydrochloride or phosphate as buffer, measured as relative content of Dimer after approximately eight weeks storage at 37° C.

Compositions comprising ethylenediamine or phosphate as buffer components were prepared following example 5 and the chemical stability of the compositions was examined according to example 6. The results (% Dimer formed) from GPC-HPLC analyses are presented in FIG. 5. As can be seen, substitution of phosphate with ethylenediamine increases the chemical stability for both human insulin and acylated insulin derivates.

The invention claimed is:

1. A pharmaceutical formulation comprising a polypeptide selected from insulin, an insulin analogue or an insulin derivate, ethylenediamine or salts thereof and an antimicrobial preservative agent.

2. A pharmaceutical formulation according to claim 1, wherein the concentration of ethylenediamine is in the range from 1-100 mM.

3. A pharmaceutical formulation according to claim 2, wherein the concentration of ethylenediamine is in the range from 1-50 mM.

4. A pharmaceutical formulation according to claim 3, wherein the concentration of ethylenediamine is in the range from 3-25 mM.

5. A pharmaceutical formulation according to claim 4, wherein the concentration of ethylenediamine is in the range from 5-16 mM.

6. A pharmaceutical formulation according to claim 1, wherein the antimicrobial preservative agent is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, thimerosal, bronopol, benzoic acid, imidurea, chlorhexidine, sodium dehydroacetate, chlorocresol, ethyl p-hydroxybenzoate, benzethonium chloride, chlorphenesine (3p-chlorphenoxypropane-1,2-diol) or a mixture thereof.

7. A pharmaceutical formulation according to claim 6, wherein the antimicrobial preservative agent is selected from the group consisting of phenol, m-cresol or a mixture thereof.

8. A pharmaceutical formulation according to claim 7, wherein the antimicrobial preservative agent is present in a concentration from 0.1 mg/ml to 20 mg/ml.

9. A pharmaceutical composition according to claim 1, wherein the polypeptide is an insulin analogue selected from the group consisting of analogues of human insulin where the amino acid residue at position B28 is Asp, Lys, Leu, Val, or Ala and position B29 is Lys or Pro; or B3 is Lys and B29 is Glu; or A21 is Gly and Arg has been added to B31 and B32; or where the amino acid residues in B28-B30 have been deleted; or where the amino acid residue at B27 has been deleted; or where the amino acid residue at B30 has been deleted.

10. A pharmaceutical composition according to claim 1, wherein the polypeptide is an insulin derivate selected from the group consisting of B29-$N^\epsilon$-tetradecanoyl-des(B30)-human insulin, B29-$N^\epsilon$-tetradecanoyl-human insulin, B29-$N^\epsilon$-hexadecanoyl human insulin, B28-$N^\epsilon$-tetradecanoyl-Lys$^{B28}$Pro$^{B29}$ human insulin, B28-$N^\epsilon$-hexadecanoyl-Lys$^{B28}$Pro$^{B29}$ human insulin, B30-$N^\epsilon$-tetradecanoyl-Thr$^{B29}$Lys$^{B30}$ human insulin, B30-$N^\epsilon$-hexadecanoyl-Thr$^{B29}$Lys$^{B30}$-human insulin, B29-$N^\epsilon$-(N-hexadecanoyl-γ-glutamyl)-des(B30)-human insulin, B29-$N^\epsilon$-(N-litocholyl-γ-glytamyl)-des(B30)-human insulin, B29-$N^\epsilon$-(ω-carboxyheptadecanoyl)-des(B30)-human insulin, $N^\epsilon$B29-tetradecanoyl des(B30) human insulin, $N^\epsilon$B28-tetradecanoyl Lys$^{B28}$Pro$^{B29}$ human insulin, $N^\epsilon$B29-tetradecanoyl Asp$^{B28}$ human insulin and Lys$^{B29}$($N^\epsilon$-hexadecandioyl-γ-Glu)-des(B30) human insulin.

* * * * *